United States Patent [19]
Franciskovich

[11] Patent Number: 5,939,022
[45] Date of Patent: Aug. 17, 1999

[54] ARTICLE FOR TRANSPORTING BIOLOGICAL SAMPLES DURING ANALYSIS

[75] Inventor: Phillip P. Franciskovich, Brown Deer, Wis.

[73] Assignee: Pharmacia Biotech, INc., Milwaukee, Wis.

[21] Appl. No.: 08/987,679

[22] Filed: Dec. 9, 1997

[51] Int. Cl.⁶ .................... B01L 11/00; G01L 33/48
[52] U.S. Cl. .................. 422/100; 422/61; 137/615
[58] Field of Search .................. 422/100–102, 422/58, 61; 137/615

[56] References Cited

U.S. PATENT DOCUMENTS

| | | | |
|---|---|---|---|
| 3,616,387 | 10/1971 | Siebert et al. | 204/180 |
| 3,755,121 | 8/1973 | Schlutz | 204/180 |
| 3,930,973 | 1/1976 | Nerenberg | 204/180 |
| 4,094,759 | 6/1978 | Ruhenstroth-Bauer et al. | 204/180 |
| 4,096,825 | 6/1978 | Golias et al. | 118/221 |
| 4,252,538 | 2/1981 | Barr | 422/102 |
| 4,455,370 | 6/1984 | Bartelsman et al. | 435/6 |
| 4,826,759 | 5/1989 | Guire et al. | 422/61 |
| 4,849,078 | 7/1989 | Love et al. | 204/182.8 |
| 5,071,746 | 12/1991 | Wilk et al. | 422/61 |
| 5,149,408 | 9/1992 | Perlman | 204/182.3 |
| 5,234,559 | 8/1993 | Collier et al. | 204/182.8 |
| 5,405,516 | 4/1995 | Bellon | 204/180.1 |
| 5,464,515 | 11/1995 | Bellon | 204/182.8 |

FOREIGN PATENT DOCUMENTS

WO 96/27787   9/1996   European Pat. Off. .

*Primary Examiner*—Lyle A. Alexander
*Attorney, Agent, or Firm*—Quarles & Brady LLP

[57] ABSTRACT

A device is able to simultaneously transport a plurality of biological samples. The device has a plurality of strips of bibulous material extending from a body of the device with a regular spacing between the strips. By manipulating the device the effective spacing between the extremities of the strips changes. This enables the strips to pick up fluid biological samples from a laboratory appliance in which the samples are located at a first spacing and then deposit the biological samples onto another laboratory appliance which accepts the samples at a different spacing. A version of the device for robotic manipulation also is disclosed.

22 Claims, 6 Drawing Sheets

ARTICLE FOR TRANSPORTING BIOLOGICAL SAMPLES DURING ANALYSIS

BACKGROUND OF THE INVENTION

The present invention relates to apparatus for transferring samples of a biological liquid, such as a fluid containing DNA, between laboratory appliances; and more particularly to such apparatus for transferring the biological liquid from a preparation tray to an electrophoresis apparatus.

Zone electrophoresis is a well known technique for analyzing various types of biological samples, such as blood, urine or DNA. The prepared biological samples are deposited onto a gel medium, cellulose acetate for example, which then is subjected to an electric field. The action of the electric field causes the proteins, which are amphoteric molecules, to ionize and linearly separate according to their respective electrical charge intensities. This provides a pattern in the gel which identifies constituents of the biological sample.

The process commences by preparing each of the samples in a tray containing a plurality of wells organized into a two dimensional matrix of rows and columns, such as the collection tray described in U.S. Pat. No. 5,603,899, which description is incorporated herein by reference. Each well may either contain a different biological sample to be analyzed or similar samples which are processed differently.

Various devices have been developed to transfer the biological samples from the wells. Examples of these devices are shown in the 3,616,387; 4,096,825; and 5,464,515 U.S. Pat. Nos. These transfer devices have a plurality of bibulous fingers which coincide in number and spacing with a row or column of wells within the preparation tray. The transfer is performed by dipping the fingers into a row or column of wells the absorbent material of the fingers pick up samples of the biological fluids. The transfer device then can be removed from the wells and repositioned with the fingers in contact with the electrophersis gel, thereby depositing the biological material at different positions onto the gel.

The separation of each sample's constituents occurs along a line between the electric poles of the electrophoresis apparatus. Automatic equipment has been developed which, in addition to separating biological samples by electrophoretic action, has linear arrays of photodetectors aligned with each separation line to detect the position of constituents along those lines. Thus, one set of photodetectors determines the distribution of the constituent material of one biological sample deposited in the gel.

Unfortunately, the spacing of the wells in commonly available processing trays does not coincide with the spacing of the linear photodetector arrays in standard electrophoresis equipment. Typically the linear photodetector arrays are more closely spaced than the tray wells, in order to maximize the number of samples processed during each operation of the electrophoresis apparatus. As a result, the fingers of the transfer device, which are spaced according to the well arrangement in the preparation tray, are not properly spaced with respect to the areas on the electrophoretic gel in which the deposits are to be made. The only solution is to utilize preparation trays with wells matched with the spacing of the photodetector arrays in the electrophoretic apparatus. However, such non-standard trays are often more expensive and may not be compatible with other devices used in preparing the biological samples. Further, if a laboratory has several types of electrophoretic equipment, different trays may have to be provided for each type.

Therefore, it is desirable to provide a transfer device which can accommodate the different spacing requirements of a variety of laboratory appliances.

SUMMARY OF THE INVENTION

A general object of the present invention is to provide an article for simultaneously transferring a plurality of biological samples from a series of wells having a first spacing to another device in which the samples must be deposited at a second spacing.

Another object is to provide such a transfer article with a plurality of strips for carrying the biological samples in which the lateral spacing of the strips may be varied so as to adjust to the different spacings.

These and other objectives are satisfied by transfer device for simultaneously transporting a plurality of biological samples. The device includes a first tab and a second tab. A plurality of strips of bibulous material for absorbing the biological samples are connected between the first and second tabs. The first and second tabs are slidable with respect to each other to adjust the plurality of strips and vary spacing between extremities of adjacent ones of the plurality of strips. Such adjustment enables the inter-extremity spacing to be varied to correspond to the spacing requirements of different pieces of laboratory equipment.

In one embodiment of the transfer device, the plurality of strips are connected together to form a helical section having first and second ends with a plurality of convolutions therebetween. Each convolution has a separate tongue of bibulous material for absorbing the biological samples. The first tab is connected to the first end of the helical section, passes through the helical section and projects from the second end. Similarly, the second tab is connected to the second end, passes through the helical section and projects from the first end. Moving the first and second tabs in relation to each other expands or contracts the helix section thereby changing spacing between the tongues.

In another embodiment of the present transfer device, each of the strips has a first section attached to the first tab with a given spacing between the first sections, and has a second section attached to the second tab with a different spacing between the second sections. An intermediate section of each strip extends between the first and second sections at an angle so that the first and second sections are offset from each other. By sliding the first and second tabs with respect to each other, the strips alternately fold at either the junction between the first section and the intermediate section or the junction between the second section and the intermediate section, thereby changing the extremity of the strip and the spacing between the extremities.

In a further embodiment, the transfer article includes a body having opposing first and second sides. A first plurality of strips, of bibulous material for absorbing biological samples, project at intervals from the first side of the body, and a second plurality of strips of the bibulous material project at intervals from the second side of the body. The strips in the second plurality are offset from the strips in the first plurality.

Elements, such as a slit and crease for example, enable the transfer article to be folded into a state in which the first plurality of strips is interdigitated with the second plurality of strips. Because of the offset between the first and second pluralities of strips, the folding results in the combined set of strips being spaced apart by one-half the spacing of only the first or second plurality of strips.

The unfolded transfer article is employed to absorb biological samples from a first laboratory appliance. In doing so, the first plurality of strips may be dipped into a row of wells in a preparation tray that contain biological samples.

Thus the first plurality of strips absorb the biological samples from those wells. Then the transfer article is flipped over and the second plurality of strips is dripped into another row of wells to absorb additional biological samples. Next the transfer article is folded essentially in half so that the first and second sides align and the two pluralities of strips become interdigitated. The folded transfer article is juxtaposed against the second laboratory appliance so that the biological samples become deposited from the first and second plurality of strips onto that appliance. This action deposits the biological samples onto the second laboratory appliance at locations that are spaced closer together than the spacing between the wells in the first laboratory appliance. This procedure can be reversed to transfer samples from an appliance with close spacing requirements to one that requires wider spacing.

DETAILED DESCRIPTION OF THE INVENTION

Figure 1:
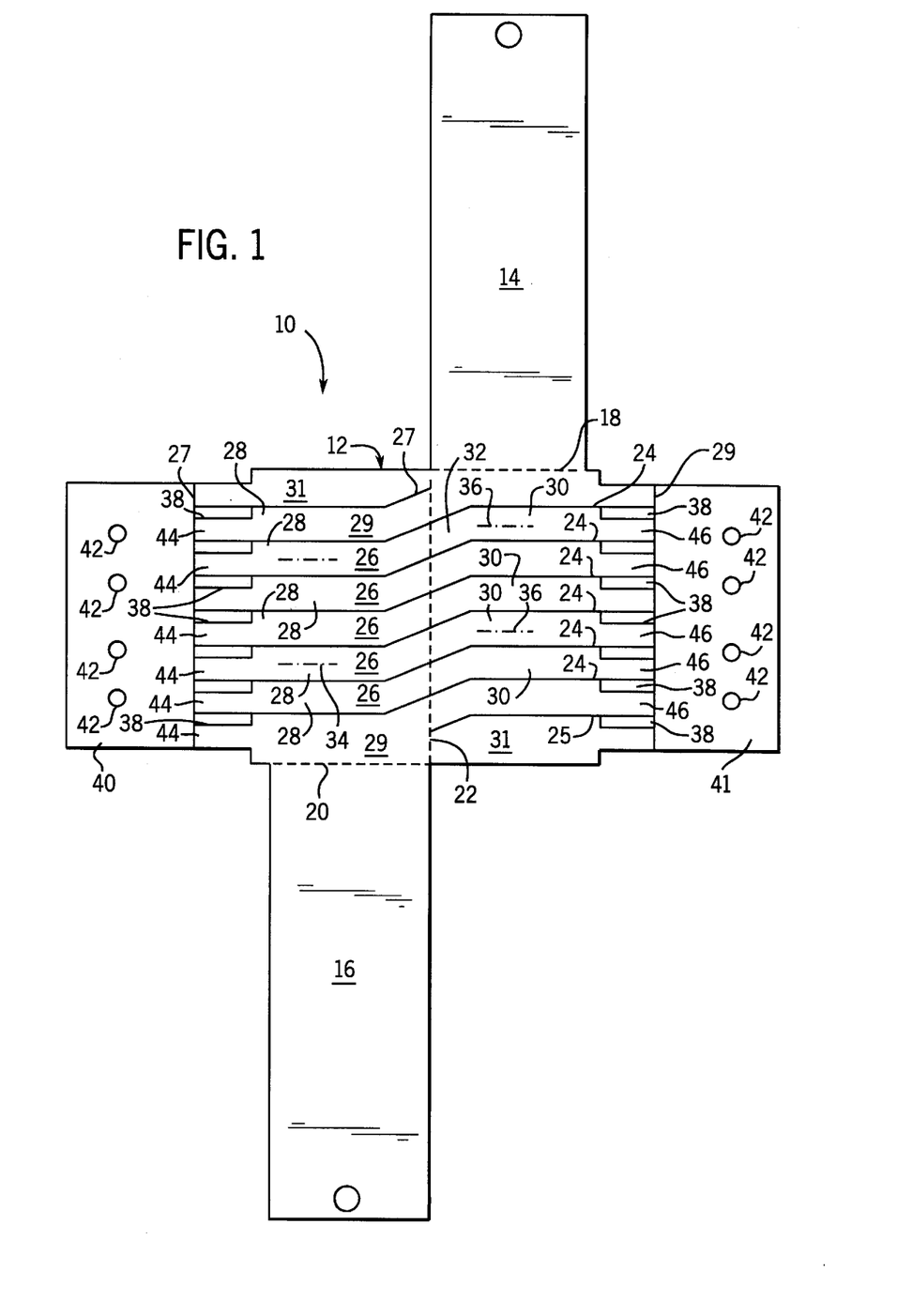
FIG. 1 is a view of a transfer article according to the present invention as it appears after being stamped from a flat piece of absorbent material.

With initial reference to FIG. 1, a transfer article 10 is stamped by a die from a sheet of bibulous material. The transfer article 10 has a central portion 12 with elongated rectangular tabs 14 and 16 extending from opposite sides thereof at linear junctions 18 and 20 indicated by dashed lines in the drawing. The central section 12 is bisected by a fold line 22, which will be described subsequently.

When the transfer article 10 is stamped, the die makes a plurality of closed linear slits 24 in the central section which are terminated at each end by parting lines 27 and 29. The slits 24 form a plurality of strips 26 therebetween which have equal widths and which are symmetrical about the fold line 22. Each of these strips 26 is divided into first and second end sections 28 and 30 interconnected by an intermediate section 32 which spans the fold line 22. Each of the end sections 28 and 30 has a central longitudinal axis 34 and 36 respectively. The intermediate sections 32 are angled with respect to each of the connected end sections so that the corresponding longitudinal axes 34 and 36 of each strip 26 are offset with respect to one another. The amount of offset is equal to the width of each of the strips 26. A first half slit 25, which is half the length of slits 24, extends from one side of the fold line 22 on one side of the array of strips 26 and a second half slit 26 extends from the other side of the fold line on the opposite side of the array of strips. The half slit 25 and 27 form outer strips 29 and 31.

The stamping also creates small rectangular voids 38 at ends of the slits 26 on both sides of the fold line 22. Absorbent tongues 44 and 46 are formed on the strips between the voids 38. The ends of the slits 24 terminate at alignment portions 40 and 41 along the edge of the transfer article 10. Each of the alignment portions 41 and 40 have a plurality of apertures 42 there through for aligning halves of the transfer article 10 upon folding as will be described.

Figure 2:
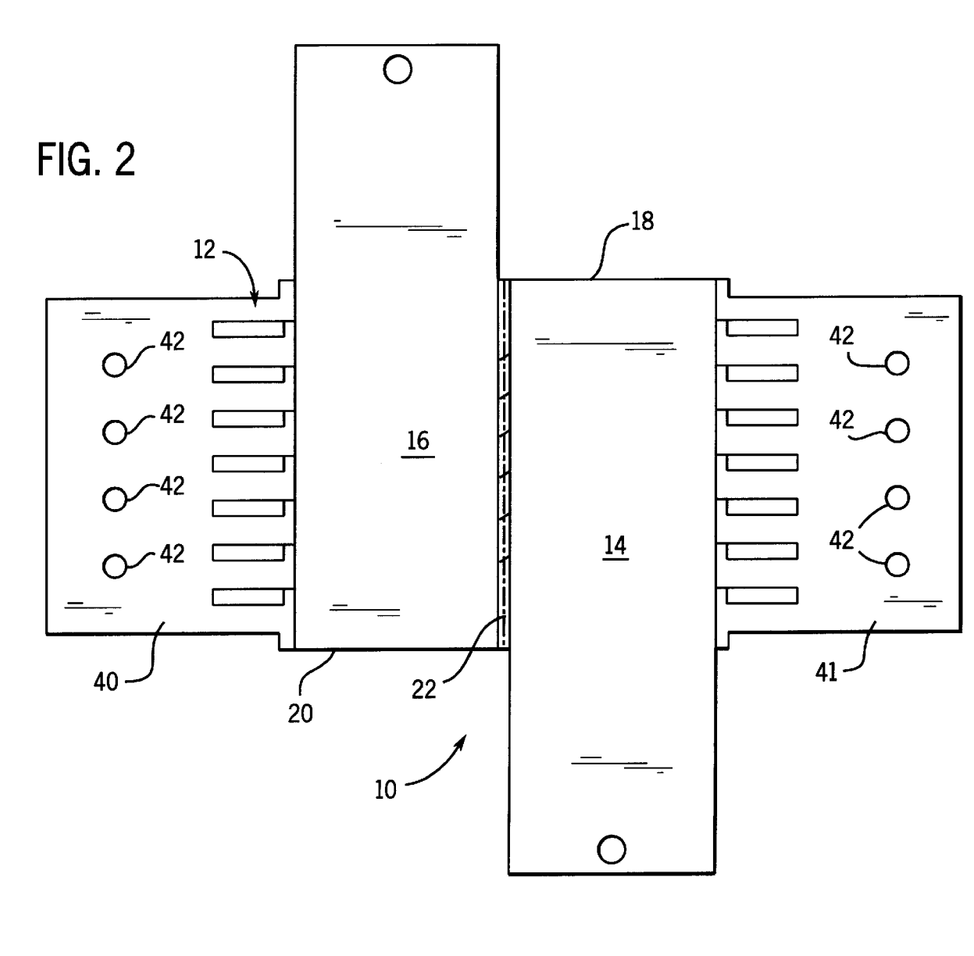
FIG. 2 depicts the transfer article in one stage of fabrication.
Figure 3:
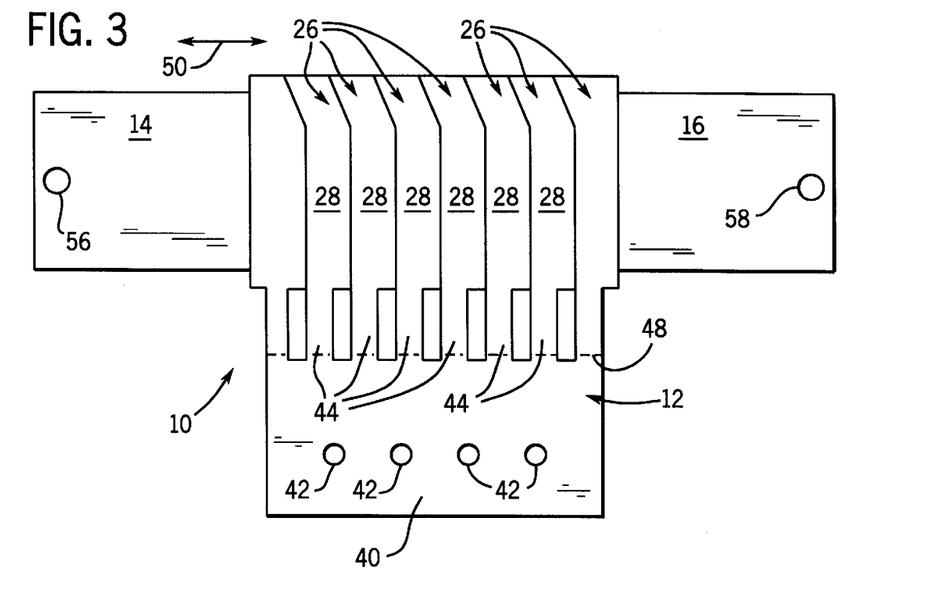
FIG. 3 depicts the transfer article in a subsequent stage of fabrication.

Once the form of the transfer article 10 has been stamped from the sheet of bibulous material, the tabs 14 and 16 are folded over the central section 12, as depicted in FIG. 2. The folds occur along junction lines 18 and 20. Then, the transfer article 10 is folded along fold line 22 until the alignment portions 40 and 41 abut with their exposed edges justified and apertures 42 aligned, as shown in FIG. 3. In this stage of fabrication, the tabs 14 and 16 are sandwiched between the end sections 28 and 30 of the plurality of strips 26 and project outward from the folded central section 12.

Plurality of strips 26 have tongues 44 and 46 at the remote ends of each of the end sections 28 and 30 which tongues form the extremities of the strips. When the transfer article 10 is folded as shown in FIG. 3, the tongues 44 on the first end sections 28 over lap the tongues 46 of the second end sections 30 at the opposite end of each strip 26. However, the first end section 28 of one strip 26 overlaps the second end section 30 of an adjacent strip 26 because of the offset provided by the angled intermediate portion 32 of each strip. These tongues 44 and 46 along with the alignment portions 40 and 41 are bonded together by applying an adhesive to their abutting surfaces.

Figure 4:
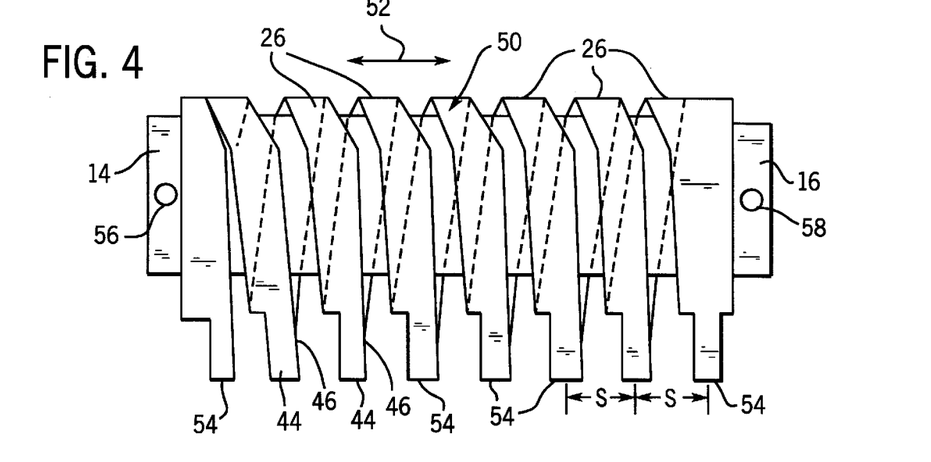
FIG. 4 depicts the transfer article in a state for use.

Once the adhesive has secured the portions of transfer article 10 together, the alignment portions 40 and 41 are detached by cutting along dashed line 48 in FIG. 3, thereby separating the plurality of strips 26 at their respective tongues 44 and 46 which are now bonded together. This bonding and separation forms the plurality of strips 26 into a flattened helix 50 as shown in FIG. 4 in which the tongue 44 of first end section 28 of each strip is bonded to the tongue 26 of the second end section 30 of another strip. Thereby each strip 26 forms a convolution of the helix 50.

The helix 50 allows the two tabs 14 and 16 to slide transversely in opposite directions as indicated by arrows 52. When the tabs 14 and 16 are pulled outward, the helix 50 closes until the extreme outward position is reached at which the array of strips 26 abut one another as shown in FIG. 3. Pushing tabs 14 and 16 into the strip helix 50 spreads apart the individual strips 26 as shown in FIG. 4. This action increases the spacing S between adjacent sets of attached tongues 44 and 46 and thus between the extremities 54 of the strips 26. As a result, the extremity spacing S can be varied to correspond to the spacing of preparation tray wells in which extremities 54 are to be dipped to absorb biological samples and then adjusted to the spacing required by the electrophoresis apparatus. The present embodiment allows an infinite number of spacings to be achieved between the two extreme positions of the tabs 14 and 16.

It is preferred that the tabs 14 and 16 have holes 56 and 58, respectively (FIGS. 3 and 4), that provide a means by which a robot arm grips and manipulates the transfer article 10. The holes 56 and 58 align the transfer article with the gripper of an automated workstation so that the necessary motions can be integrated into a variety of high throughput biological sample handling routines and replicated efficiently time after time. A bar code also may be affixed to the transfer article 10 thereby allowing the computer controlling the robot arm to identify the biological samples being carried.

Figure 5:
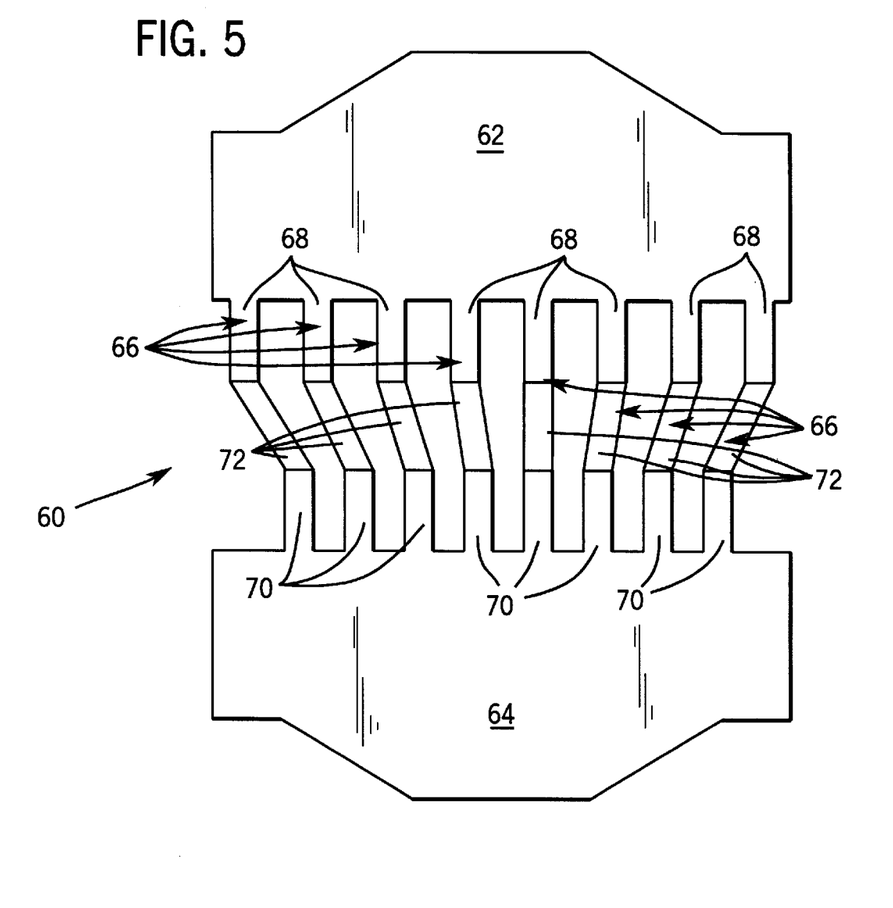
FIG. 5 depicts a second embodiment of the present invention as it appears upon being stamped from a flat sheet of absorbent material.

FIG. 5 depicts an alternative embodiment of a transfer article 60 which can be adjusted to accommodate different laboratory apparatus by sliding parts of the transfer article with respect to each other. This transfer article 60 also is stamped from a flat sheet of bibulous material. That operation forms two tabs 62 and 64 with a plurality of strips 66 connected there between. The strips 66 have a first end section 68 extending from the first tab 62 and spaced apart by a first distance. The strips 66 have a second end section 70 that extends from the second tab 64 and spaced apart by a second distance which is smaller than the first distance, i.e. the second end sections are more closely spaced than the first end sections. The respective spacing of the two strip end sections 68 and 70 correspond to the spacing of two laboratory appliances (e.g. a well tray and an electrophoresis instrument) with which the transfer article 60 is intended for use.

Figure 6:
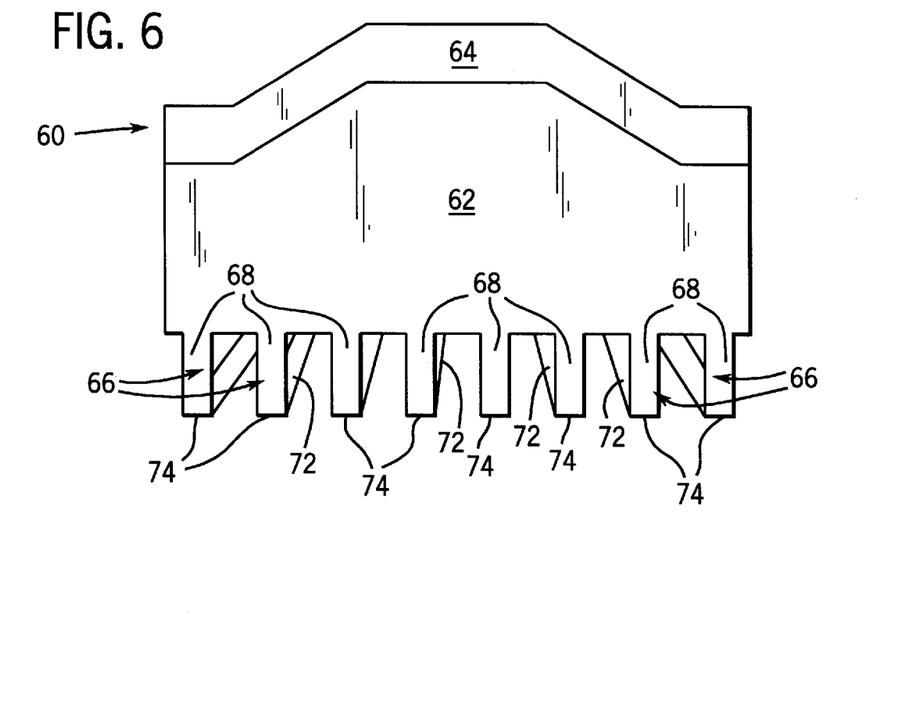
FIG. 6 shows the second embodiment of the transfer article in a first state during usage.

Each of the first end sections 68 is coupled to a different one of the second end sections 70 by an intermediate section 72. Creases are formed between the first end sections 68 and the intermediate section 72, as well as between the second end sections 70 and the intermediate section 72 thereby enabling the transfer article to be folded at each end of the intermediate section 72. FIG. 6 illustrates the transfer article 60 folded at the creases between the first end section 68 and the intermediate section 72 with major surfaces of the two tabs 62 and 64 abutting. In this orientation the extremities 74 of the strips 66 have a first spacing as determined by the distance between the first end sections 68.

Figure 7:
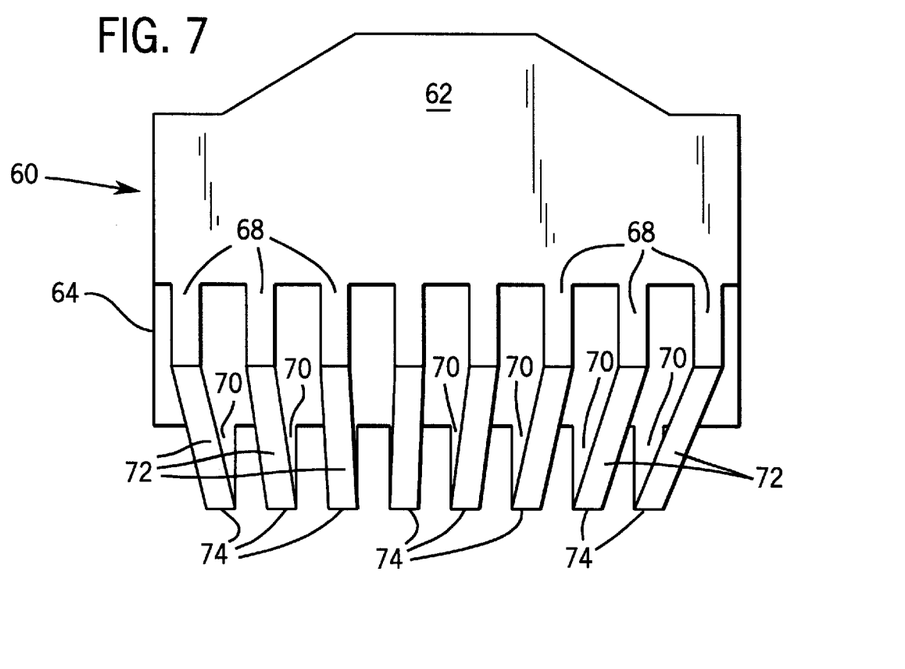
FIG. 7 depicts the second transfer article in a second state during usage.

By sliding the two tabs 62 and 64 against each other into a position shown in FIG. 7, the spacing between the extremities 74 of the strips 66 is altered to coincide with the spacing required by a different laboratory apparatus. This sliding action causes the strips 66 to unfold at the crease between their first end section 68 and intermediate section 72 and fold at the crease between the second end section 70 and the intermediate section 72. In this state, the extremities 74 are formed by the fold between each second end section 70 and intermediate section 72. Because the second end sections 70 are closer together, the spacing between the extremities 74 changes.

Thus by sliding the tabs 62 and 64 of transfer article 60 into the position of FIG. 6, biological material can be acquired from or deposited into a laboratory appliance at a wide spacing; whereas the position of FIG. 7 enables the biological material to be acquired from or deposited into an appliance at a narrower spacing. Therefore the transfer article 60 can be used to simultaneously exchange a plurality of biological samples between two laboratory appliances with different spacing requirements.

Figure 8:
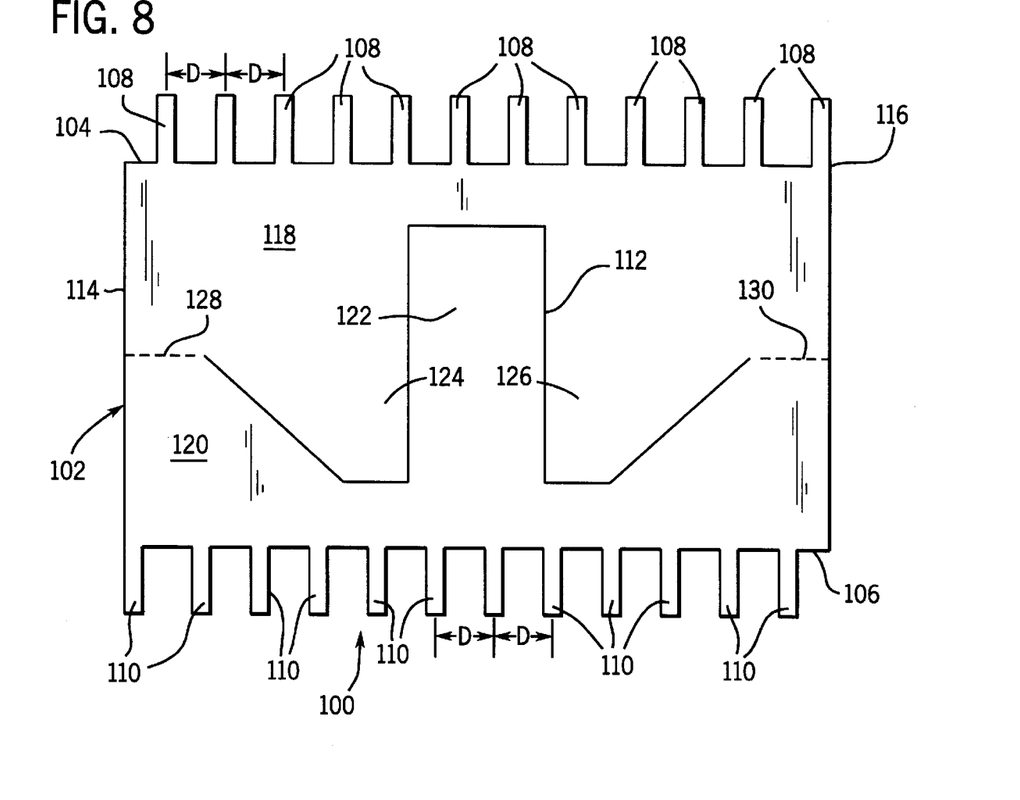
FIG. 8 is a view of a third embodiment of a transfer article according to the present invention in a flat state for use.

With initial reference to FIG. 8, a transfer article 100 is stamped by a die from a flat sheet of bibulous material. The stamping forms a rectangular body 102 having opposing edges, or sides 104 and 106. A first plurality of strips 108 project outward from the first side 104 and are uniformly spaced apart by a given center-to-center distance D, for example 9 mm. A second plurality of strips 110 project outward from the second side 106 and are uniformly spaced apart by the given center-to-center distance D. This distance D is chosen to correspond to spacing requirements of a first type of laboratory appliance, as will be described. Each strip in both the first and second the plurality of strips 108 and 110 has a width that is less than distance D. The first plurality of strips 108 is not aligned with the second plurality of strips 110, instead the two pluralities are offset by half the given center-to-center distance D, for example by 4.5 mm.

When the transfer article 100 is stamped, the die makes a closed slit 112 in the rectangular body 102. The slit is spaced the same amount from the lateral sides 114 and 116 of the body which extend between the opposing sides 104 and 106. The ends of the slit 112 are positioned equidistantly from the opposing sides 104 and 106. The slit 112 divides the rectangular body 102 into a first portion 118 from which the first plurality of strips 108 extend and a second portion 120 from which the second plurality of strips 110 project. The pattern of the slit 112 forms a rectangular tab 122 of the second portion 120 and two tapered tabs 124 and 126 of the first portion 118.

Figure 9:
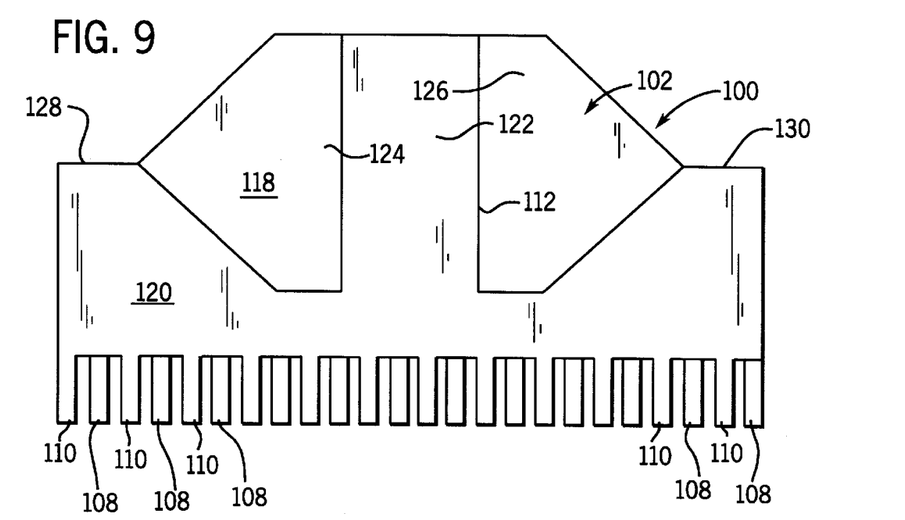
FIG. 9 depicts the third embodiment in a folded state for use.

A pair of ceases, indicated by dashed lines 128 and 130 are formed along the center line of the rectangular body 102 between each end of slit 112 and the adjacent lateral side 114 or 116. The slit 112 and pair of ceases 128 and 130 facilitate folding the transfer article 100 essentially in half, as illustrated in FIG. 9. In this folded state, the two opposing sides 104 and 106 are aligned and because of the offset in spacings, the first and second pluralities of strips 108 and 110 are interdigitated, or interleaved. Thus each one of the first plurality of strips 108 is between a different pair of the second plurality of strips 110 and each one of the second plurality of strips 110 is between two of the first plurality of strips 108, except for one strip at the end of each plurality. In this folded state, the rectangular tab 122 of the second portion 120 and the two tapered tabs 124 and 126 of the first portion 118 form a handle by which a user can grasp the transfer device remote from the strips 108 and 110.

The center-to-center distance D by which the strips 108 and 110 are spaced apart corresponds to the spacing required by the one type of laboratory appliance, such as a multiple well preparation tray for processing biological samples. When using the transfer article 100, a laboratory technician takes the article in the flat state, as shown in FIG. 8, and dips one of the pluralities of strips 108 or 110 into a row of wells in the preparation tray. Each strip enters a different well and absorbs some of the fluid biological sample therein. The technician then flips the transfer article 100 over and dips the other plurality of strips 108 or 110 into another row of wells in the preparation tray so that those strips absorb fluid biological samples.

Next the technician folds the transfer article 100 along ceases 128 and 130 into the shape shown in FIG. 9. When major surfaces of the two portions 118 and 120 of the article abut, the two pluralities of strips 108 and 110 become interdigitated with a strip-to-strip spacing of half that of the unfolded article. Therefore, the strips 108 and 110 bearing the samples now are closer together, having a spacing that conforms to that required by a second laboratory appliance, such as an automatic electrophoresis apparatus. The folded transfer article 100 then deposits the biological samples from the strips 108 and 110 onto that second laboratory appliance.

One skilled in the art will appreciate that the opposite process can be used to transfer biological materials from an appliance with very close spacings to one having wider spacing requirements. In this case, the folded article would be used to absorb the biological material and then be unfolded for depositing the material onto the second laboratory appliance. In which case material on one of the pluralities of strips 108 or 110 would first be deposited and then the transfer article 100 would be flipped over to deposit material from the other the plurality of strips 108 or 110 into the second laboratory appliance.

The foregoing description is directed primarily to preferred embodiments of the invention. Although some attention was given to various alternatives within the scope of the invention, it is anticipated that skilled artisans will likely realize additional alternatives that are now apparent from the disclosure of those embodiments. Accordingly, the scope of the invention should be determined from the following claims and not limited by the above disclosure.

I claim:

1. An article for simultaneously transporting a plurality of biological samples, wherein the article comprises:
   a body;
   a plurality of strips of bibulous material for absorbing the plurality of biological samples and extending from the body, each of the plurality of strips having an extremity; and
   a member coupled to the body for engagement by an external manipulator and which upon manipulation by the external manipulator changes a shape of the body which varies a spacing between extremities of the plurality of strips.

2. An article for simultaneously transporting a plurality of biological samples, wherein the article comprises:
   a first tab;
   a second tab; and
   a plurality of strips of bibulous material for absorbing the plurality of biological samples and being connected between the first tab and the second tab, each of the plurality of strips having at least one extremity; and
   wherein the first tab and the second tab are slidable with respect to each other to adjust the plurality of strips to provide variation of a spacing between extremities of adjacent ones of the plurality of strips.

3. The article as recited in claim 2 wherein each of the plurality of strips has a first section with a first longitudinal axis, a second section with a second longitudinal axis, and an intermediate section extending at an angle between the first section and the second section wherein the first longitudinal axis is offset from the second longitudinal axis.

4. The article as recited in claim 2 wherein each of the plurality of strips has a first section attached to the first tab, a second section attached to the first tab, and an intermediate section extending between the first section and the second section, wherein there is a first spacing between the first section of adjacent ones of the plurality of strips and a second spacing between the second section of adjacent ones of the plurality of strips.

5. The article as recited in claim 4 wherein the intermediate section is attached to the first section at a first junction and to the second section at a second junction; and wherein the first and second tabs overlap wherein sliding the first and second tabs with respect to each other folds the plurality of strips alternately at the first and second junction.

6. The article as recited in claim 2 wherein each of the plurality of strips has a first section with a first longitudinal axis and a first end portion, a second section with a second longitudinal axis and a second end portion, and an intermediate section joining the first section to the second section wherein the first longitudinal axis is offset from the second longitudinal axis, the plurality of strips being placed side-by-side in an array and folded at the intermediate section so that the first end portion of each strip overlaps with and is attached to the second end portion of an adjacent strip.

7. The article as recited in claim 6 wherein:
   the first tab is connected to the first section of a strip at a first end of the array, the first tab extends between the first and second sections of the plurality of strips and projects outward from a second end of the array;
   the second tab is connected to the second section of a strip at the second end of the array, the second tab extends between the first and second sections of the plurality of strips and projects outward from the first end of the array; and
   the first and second tabs being movable into and out of the array to change a spacing between the plurality of strips.

8. An article for simultaneously transporting a plurality of biological samples, wherein the article comprises:
   a helical section having a first end and a second end with a plurality of convolutions therebetween, and having a plurality of tongues of bibulous material for absorbing the plurality of biological samples with each tongue being attached to a different one of the plurality of convolutions;
   a first tab connected to the first end, passing through the helical section and projecting from the second end; and
   a second tab connected to the second end, passing through the helical section and projecting from the first end;
   wherein movement of the first and second tabs in relation to each other changes spacing between the plurality of tongues.

9. The article as recited in claim 8 wherein helical section comprises a plurality of strips, each having a first end and a second end, wherein the second section of each strip is attached to the first section of another strip.

10. The article as recited in claim 9 wherein a different one of the plurality of tongues is attached to one of the first and second sections of each strip.

11. An article for simultaneously transporting a plurality of biological samples, wherein the article comprises:
   a plurality of strips of bibulous material for absorbing the plurality of biological samples, each of the plurality of strips having a first section with a first longitudinal axis and a first end portion, a second section with a second longitudinal axis and a second end portion, and an intermediate section joining the first section to the second section wherein the first longitudinal axis is offset from the second longitudinal axis; the plurality of strips being placed side-by-side in an array and folded at the intermediate section so that the a first end portion each strip overlaps and is attached to the second end portion of an adjacent strip;
   a first tab connected to the first section of a strip at a first end of the array, the first tab extending between the first and second sections of the plurality of strips and projection outward from a second end of the array; and
   a second tab connected to the second section of a strip at the second end of the array, the second tab extending between the first and second sections of the plurality of strips and projection outward from the first end of the array;
   the first and second tabs being movable with respect to each other to change a spacing between the plurality of strips.

12. A method for transporting a plurality of biological samples simultaneously between first and second appliances:
   juxtaposing a transfer article with respect to the first appliance, wherein the transfer article has a plurality of strips of bibulous material which absorb the plurality of biological samples from the first applicance;
   moving first and second tabs attached to the a plurality of strips which movement changes spacing between extremities of adjacent ones of the plurality of strips; and then juxaposing the transfer article with respect to the second applicance which deposits the plurality of biological samples onto the second applicance.

13. An article for simultaneously transporting a plurality of biological samples, wherein the article comprises:

a body having opposing first and second sides;

a first plurality of strips of bibulous material for absorbing biological samples, wherein the first plurality of strips are spaced apart and project from the first side of the body; and a second plurality of strips of bibulous material for absorbing biological samples, wherein the second plurality of strips are spaced apart and project from the second side of the body with the second plurality of strips being offset from the first plurality of strips;

wherein the body is foldable into a state in which the is first plurality of strips is interdigitated with the second plurality of strips.

14. The article as recited in claim 13 wherein the body has a slit which defines two portions of the body that become folded against one another to interleave the first and second pluralities of strips.

15. The article as recited in claim 14 wherein the body further comprises first and second lateral sides extending between the first and second sides, and a slit separated from the first and second sides and from the first and second lateral sides.

16. The article as recited in claim 15 wherein the body further comprises a first crease extending between the slit and the first lateral side; and a second crease extending between the slit and the second lateral side.

17. A method for transporting a plurality of biological samples simultaneously between first and second appliances using a transfer article having a first portion from which project a first plurality of strips of bibulous material and a second portion from which project a second plurality of strips of bibulous material, the method comprising:

juxtaposing the transfer article with respect to the first appliance whereby the first and second plurality of strips absorb biological samples from the first appliance;

moving the first portion of the transfer article with respect to the second portion thereby changing a spacing between adjacent ones of the first and second pluralities of strips; and juxtaposing the transfer article with respect to the second appliance which deposits biological samples from the first and second plurality of strips onto the second appliance.

18. The method as recited in claim 17 wherein juxtaposing the transfer article with respect to the first appliance comprises:

juxtaposing the first portion of a transfer article with respect to the first appliance, wherein the first plurality of strips absorb biological samples from the first appliance; and then juxtaposing the second portion of a transfer article with respect to the first appliance, wherein the second plurality of strips absorb additional biological samples from the first appliance.

19. The method as recited in claim 18 wherein moving the first portion of the transfer article with respect to the second portion comprises folding the transfer article so that the first plurality of strips are interdigitated with the second plurality of strips.

20. The method as recited in claim 17 wherein:

juxtaposing the transfer article with respect to the first appliance comprises folding the transfer article so that the first plurality of strips are interdigitated with the second plurality of strips; and moving the first portion of the transfer article with respect to the second portion comprises unfolding the transfer article.

21. The method as recited in claim 20 wherein juxtaposing the transfer article with respect to the second appliance comprises:

juxtaposing the first portion of a transfer article with respect to the first appliance, wherein the first plurality of strips deposits biological samples onto the second appliance; and then juxtaposing the second portion of a transfer article with respect to the first appliance, wherein the second plurality of strips deposits biological samples onto the second appliance.

22. A method for transporting a plurality of biological samples simultaneously between first and second appliances:

juxtaposing a first side of a transfer article with respect to the first appliance, wherein the first side has a first plurality of strips of bibulous material which absorb biological samples from the first appliance;

juxtaposing a second side of a transfer article with respect to the first appliance, wherein the second side has a second plurality of strips of bibulous material which absorb additional biological samples from the first appliance;

folding the transfer article so that the first plurality of strips are interdigitated with the second plurality of strips; and after folding, juxtaposing the transfer article with respect to the second appliance which deposits biological samples from the first and second plurality of strips onto the second appliance.

* * * * *